US011666207B1

(12) United States Patent
Chen et al.

(10) Patent No.: US 11,666,207 B1
(45) Date of Patent: Jun. 6, 2023

(54) MULTIFUNCTIONAL COMPOUND LIGHT PENETRATION ENHANCED IMAGING SYSTEM AND ENHANCED IMAGING METHOD

(71) Applicant: Qingdao Yuren Medical Technology Co., Ltd., Qingdao (CN)

(72) Inventors: Yong Chen, Qingdao (CN); Xuexiao Ma, Qingdao (CN); Xibin Yang, Qingdao (CN); Zhongwei Gu, Qingdao (CN); Feng Lin, Qingdao (CN); Hongjuan Wang, Qingdao (CN)

(73) Assignee: Qingdao Yuren Medical Technology Co., Ltd., Qingdao (CN)

( * ) Notice: Subject to any disclaimer, the term of this patent is extended or adjusted under 35 U.S.C. 154(b) by 0 days.

(21) Appl. No.: 17/882,255

(22) Filed: Aug. 5, 2022

(30) Foreign Application Priority Data

Dec. 23, 2021 (CN) .......................... 202111594036.3

(51) Int. Cl.
*A61B 1/05* (2006.01)
*A61B 1/00* (2006.01)

(52) U.S. Cl.
CPC ............ *A61B 1/05* (2013.01); *A61B 1/00096* (2013.01)

(58) Field of Classification Search
CPC .............................. A61B 1/05; A61B 1/00096
See application file for complete search history.

(56) References Cited

U.S. PATENT DOCUMENTS

| 6,936,001 | B1* | 8/2005 | Snow | A61B 17/02 600/235 |
| 2008/0027279 | A1* | 1/2008 | Abou El Kheir | A61B 1/05 600/173 |
| 2010/0022838 | A1* | 1/2010 | Hoeg | A61B 1/00096 600/131 |
| 2012/0190917 | A1* | 7/2012 | Ohdaira | A61B 17/068 600/32 |
| 2014/0107427 | A1* | 4/2014 | Chow | A61M 25/0108 600/249 |
| 2014/0357952 | A1* | 12/2014 | Krohn | A61B 1/00006 600/112 |
| 2022/0240917 | A1* | 8/2022 | Sun | A61B 17/06 |

* cited by examiner

*Primary Examiner* — Jonathan R Messmore
(74) *Attorney, Agent, or Firm* — Nitin Kaushik

(57) ABSTRACT

The present invention belongs to the technical field of medical instruments, and discloses a multifunctional compound light penetration enhanced imaging system and an enhanced imaging method. The structural design of the present invention is reasonable. Through the cooperation of the first working channel tube, the second working channel tube, and the third working channel tube, the size of the channel is switched. When the system shrinks to the minimum, the opening size of the wound is only 1/3 of that when the system is fully opened, which is suitable for a double-channel spinal endoscopic surgery. When the system is expanded to the maximum, it is suitable for transforaminal endoscopic surgery, and is suitable for multiple surgical modes. By adding a special red light component on the basis of the white light to form compound light illumination and increase the system transmittivity, the background penetration is realized.

8 Claims, 15 Drawing Sheets

(a)

(b)

MULTIFUNCTIONAL COMPOUND LIGHT PENETRATION ENHANCED IMAGING SYSTEM AND ENHANCED IMAGING METHOD

CROSS-REFERENCE TO RELATED APPLICATIONS

The application claims priority to Chinese patent application No. 202111594036.3, filed on Dec. 23, 2021, the entire contents of which are incorporated herein by reference.

TECHNICAL FIELD

The present invention belongs to the technical field of medical instruments, and more particularly relates to a multifunctional compound light penetration enhanced imaging system and an enhanced imaging method.

BACKGROUND

At present, the endoscopic imaging technology has been widely used in the clinic, and the endoscopic imaging system includes a lighting device, an electronic endoscope, and a processor device.

At present, the endoscopic system with the narrow-band imaging function is expensive and has a low popularization rate. Moreover, the narrow-band imaging technique must be used in combination with a special camera device to realize image contrast enhancement through special image processing, and can not be used in combination with the common endoscopic imaging system, i.e. the physical properties of the narrow-band light to interact with hemoglobin, the main light-absorbing substance in blood vessels, are used to enhance the morphology of intramucosal blood vessels. Taking the Olympus narrow-band imaging system as an example, a narrow-band rotary optical filter is added at the rear end of the white light source so as to generate the narrow-band light, and the examined part is illuminated and imaged. That is, at a certain moment, a certain monochromatic light illuminates the tissue, and at the next moment, another monochromatic light illuminates the tissue, so as to obtain images under illumination conditions at different moments, and then the color enhancement is realized through algorithmic synthesis. The disadvantage of this technique is the need to illuminate the tissue with different colors at different moments and then perform image synthesis, which does not allow simultaneous illumination imaging, increases the imaging time, and sacrifices the imaging speed. In addition, in endoscopic surgery, different endoscopic surgeries need to be matched with different endoscopic sheaths, and the endoscopic sheaths on the market have a single function. It is therefore desirable to invent a multi-functional imaging apparatus that does not sacrifice the imaging speed and simplifies the image processing procedure.

Through the above analysis, the problems and defects of the prior art are that (1) the existing endoscopic imaging apparatuses are expensive, cannot achieve simultaneous illumination imaging, and have long imaging time and slow imaging speed; (2) at the same time, the matched endoscopic sheath has a single function, and the single working baffle plate has a certain size, which can only be used for a single operation; (3) camera lens in the fluid has a poor definition, especially in a bleeding state, and the microscopic view is blurred, affecting the surgical operation.

The difficulty of solving the above problems and defects is that since at present, narrow-band imaging is the way to enhance the imaging effect on the market, firstly, the imaging manner needs to be combined with a dedicated camera device to achieve image contrast enhancement through special image processing such that it is complicated to operate, expensive and can not be combined with the common endoscopic imaging system; secondly, this technique needs to illuminate the tissue with different colors at different moments and then perform image synthesis, which can not achieve simultaneous illumination imaging, thereby increasing the imaging time and sacrificing the imaging speed; finally, in endoscopic surgery, the endoscope needs to match a corresponding endoscopic sheath, and the endoscopic sheath on the market has a single function.

The significance of solving the above problems and defects is that the technical features of the present invention are that on the basis of illuminating white light, the illuminating light of a red light source is added to simultaneously irradiate onto an object without time-sharing illumination, and then an algorithm is used to perform image synthesis to obtain an enhanced image; during the operation, when the bleeding at the tissue to be tested blocks the sight, the fluid mixed with the blood appears red, with the minimum absorption for red light and the maximum absorption for other colors such as blue light; at this moment, the red light component penetrates through the fluid mixed with the blood, irradiates onto the tissue, and is then reflected, and then penetrates through the fluid mixed with the blood again, and undergoes imaging by a camera device such that the added red light has the minimum component loss so as to realize the enhanced penetration of the fluid and realize a good imaging effect without sacrificing the imaging speed and simplifying the image processing flow; it can realize the enhanced image effect without changing the current machine structure but only changing the illuminating light source; in addition, when the system is contracted to the minimum, the opening size of wound is only 1/3 of that when the system is fully opened, so it is suitable for a double-channel spinal endoscopic surgery; when the system is expanded to the maximum, it is suitable for a transforaminal endoscopic surgery, so as to adapt to multiple surgical modes.

SUMMARY

In response to the problems of the prior art, the present invention provides a multifunctional compound light penetration enhanced imaging system and an enhanced imaging method.

The present invention is realized in that a multifunctional compound light penetration enhanced imaging system is provided, wherein the multifunctional compound light penetration enhanced imaging system is provided with a first working baffle plate, a second working baffle plate, and a third working baffle plate; the second working baffle plate is clamped on an outer side of the first working baffle plate; the third working baffle plate is slidably inserted in an inner cavity of the second working baffle plate.

Further, the multifunctional compound light penetration enhanced imaging system is provided as follows:
the first working baffle plate is composed of an endoscopic sheath, an endoscopic channel, a flushing and sucking channel, a first sliding groove, a first limiting plate, a first extension channel, a first groove, a first through-hole, a second groove, a handle, a rotating shaft, a gear, and a knob; the outer side of the first working baffle plate is clamped with a second working baffle plate; the second working baffle plate is composed of a first baffle plate, a first opening groove, a first sliding block, a second sliding groove, a first extension plate, a limiting column, a second opening groove, and a rack; the third working baffle plate is slidably inserted into the inner cavity of the second working baffle plate; the third working baffle plate is composed of a second baffle, a second sliding block, a second limiting plate, and a limiting groove.

The inner wall and the outer wall of the first working baffle plate, the second working baffle plate, and the third working baffle plate are all circular arc-shaped; a rotating shaft is inserted into the first through-hole, a gear is fixedly connected to the rotating shaft in the second groove, and a knob is fixedly connected to an upper end of the rotating shaft; the endoscopic sheath, the first baffle plate, and the second baffle plate can slide against each other therebetween and are coaxial, and the inner diameter size of a combined opening is between 130 degrees and 360 degrees.

Further, the endoscopic sheath is composed of an upper and a lower part; the lower part of the endoscopic sheath is a semi-arc shape symmetrical up and down and has a crescent-shaped cross section;
a lower end of the upper part of the endoscopic sheath coincides with the lower part of the endoscopic sheath, and an outer diameter of the upper end of the upper part of the endoscopic sheath is 1 times the outer diameter of the lower end of the upper part of the endoscopic sheath, and an arc radian of the outer side of the upper part of the endoscopic sheath is 130 degrees;
a through endoscopic channel is provided in the center of the upper end face and the lower end face of the endoscope sheath, and arc-shaped flushing and sucking channels are symmetrically provided on the left and right with the endoscopic channel as the center;
a first groove is provided at the outer end of the contact position of the upper part and lower part of the endoscopic sheath, a second groove is provided at the front end of the first groove to the rear, a first through-hole is provided at the upper end and lower end of the second groove, the upper end of the first through-hole is flush with the upper end face of the endoscopic sheath, a rotating shaft is inserted into the first through-hole, and a gear is fixedly connected to the rotating shaft in the second groove; the height of the outer side of the gear is between the first groove and the outer side of the lower part of the endoscopic sheath; the knob is fixedly connected to the upper end of the rotating shaft penetrating out of the first through-hole;
the upper side and lower side of the outer end of the endoscopic sheath are symmetrically provided with a first sliding groove which is opened outwards, the longitudinal section of the first sliding groove is T-shaped, the first sliding groove takes the right rear end face of the endoscopic sheath as a starting point, and rotates clockwise (see FIG. 2) around the center of a circle for 128 degrees to reach an ending point; the upper end and lower end of the first sliding groove are symmetrically provided with first extension channels; the first extension channel takes the right rear end face of the endoscopic sheath as the starting point, and the first sliding groove, which rotates 5 degrees clockwise (see FIG. 2) around the center of a circle to reach the ending point, is fixedly connected with the first limiting plate inside, and the outer side of the first limiting plate is flush with the outer side of the endoscopic sheath.

Further, the first baffle plate is a circular arc-shaped long plate and the inner diameter of the first baffle plate is the same as the outer diameter of the endoscopic sheath; the inner side of the first baffle plate takes a left rear end face of the inner side of the first baffle plate as the starting point and rotates counterclockwise (see FIG. 2) around the center of a circle by 125 degrees to the ending point where a first sliding block having a T-shaped longitudinal section is fixedly connected; the first sliding block is symmetrical up and down, and a first extension plate is fixedly connected symmetrically at the upper end and lower end of a left rear side of the first sliding block, and the first sliding block is adapted to a first sliding groove and is clamped therein, and the first extension plate is adapted to the first extension channel and is clamped therein;
the first baffle plate takes a left rear end face of the first baffle plate as the starting point and rotates counterclockwise (see FIG. 2) around the center of a circle by 120 degrees to the ending point, a first opening groove is provided on the inner side of the first baffle plate, and the upper end and lower end of the first opening groove on a left rear side are both fixedly connected with a limiting column; a second sliding groove is provided on the outer side of the first sliding block, and the second sliding groove is in communication with the first opening groove, and the first sliding block takes a left rear end face of the first sliding block as the starting point and rotates counterclockwise (see FIG. 2) around the center of a circle by 5 degrees to the ending point where a second opening groove is provided;
the rack is fixedly connected to the inner side of the upper end of the first baffle plate, and the rack meshes with the gear.

The second baffle plate is similar in shape to the first opening groove and the second baffle plate is inserted into the first opening groove;
the second sliding block is fixedly connected to the upper end and lower end of the inner side of the second baffle plate, and the second sliding block is clamped in the second sliding groove; the second sliding block takes a right rear end face of the second baffle plate as the starting point and rotates counterclockwise (see FIG. 2) around the center of a circle by 5 degrees to the ending point where a second limiting block is fixedly connected, and the second limiting block is adapted to a size and shape of the second opening groove and can be clamped in the second opening groove;
the second baffle plate takes the left rear end face thereof as the starting point and rotates clockwise (see FIG. 2) around the center of a circle by 1 degree to the ending point where a limiting groove is provided at the upper end and lower end of the ending point, and the limiting column is clamped in the limiting groove.

Further, the multifunctional compound light penetration enhanced imaging system is further provided with
a first fixing device, a second fixing device, a third fixing device, a compound illuminating device, a camera device, and a connecting wire;
wherein the first fixing device is composed of a first fixing plate, an internal thread hole, and a second through-hole;
the second fixing device is composed of a second fixing plate, a third through-hole, a fourth through-hole, a third fixing plate, and a first routing hole;
a first routing hole is provided in the middle of the third fixing device;
the compound illuminating device is composed of an LED lamp, an L-shaped line tube, an optical fibre, a control box, a first light combining element, a red light source, a first lens, a second light combining device, a second lens, a primary color light source, and a coupling device;

the camera device is composed of a camera lens, an insulating sleeve, an image sensor, a receiving plate, a second routing hole, a PCB board, a shielding can, and a signal cable.

Further, the first fixing plate has the same shape and size as the upper end of the endoscopic sheath and is fixedly connected to the upper end of the endoscopic sheath; the internal thread hole is provided in the middle of the first fixing plate, and the second through-holes are symmetrically provided on the left side and right side of the first fixing plate; the internal thread hole corresponds to the endoscopic channel and a second channel is located directly above a second flushing and sucking channel;

a general medical water receiving valve is fixedly connected in the second through-hole, and an endoscope fixing device is threadedly connected in the internal thread hole; the endoscope fixing device is composed of a lower fixing cylinder, a clamping block, an upper fixing cylinder, an L-shaped clamping groove, and a fifth through-hole;

the lower fixing cylinder is a cylinder provided with an external thread line at the outer end of the lower side, and a thread of the cylinder is connected in the internal thread hole;

a clamping block is symmetrically fixedly connected at the front side and rear side of the inner end of the upper part of the lower fixing cylinder; the outer diameter of the upper fixing cylinder is the same as that of the lower fixing cylinder, and a fifth through-hole is provided in the middle of the upper end of the upper fixing cylinder; the L-shaped clamping groove is symmetrically arranged at the center of the front end and rear end of the lower side of the upper fixing cylinder, and the clamping block is clamped in the L-shaped clamping groove; the upper fixing cylinder is fixedly connected to the upper end of an outer cylinder, and a protecting window is fixedly connected to the inner side of the lower end of the outer cylinder.

Further, the second fixing plate and the third fixing plate are both circular plates and the outer diameter thereof is the same as the inner diameter of the outer cylinder, the second fixing plate is fixedly connected to the outer cylinder at the upper end of the protecting window, the front end of the second fixing plate is provided with a fourth through-hole, and the rear end of the second fixing plate is symmetrically provided with two third through-holes on the left and right; an insulating sleeve is sleeved on the outer side of an intermediate assembly of the second fixing plate and the third fixing plate.

Further, the lower end of the camera lens is clamped in the fourth through-hole and the upper end of the camera lens is electrically connected to the image sensor;

the image sensor is fixedly connected to a receiving plate and is electrically connected to a PCB board, and an outer end of the image sensor is sleeved with shielding can, the lower end of the PCB board is electrically connected to a signal cable, and the upper end of the signal cable is inserted into a connecting wire through the first routing hole;

two LED lamps are provided and are respectively clamped in the third through-hole and the upper end of the LED lamp is electrically connected with an optical fibre;

the optical fibre passes through the L-shaped line tube at the left end and right end of the insulating sleeve and is electrically connected to the control box;

the control box is provided therein with a first light combining element, a red light source, a first lens, a second light combining device, a second lens, a primary color light source, and a coupling device;

intensities of the primary color light source and the red light source are adjustable; the right side of the primary color light source is successively provided with a second lens, a second light combining element, a first light combining element, and a coupling device;

the upper end of the first light combining element is successively provided with a first lens and a red light source; the first light combining element and the second light combining element are both dichroscopes; the optical fibre is connected to the right side of the coupling device.

Further, the insulating sleeve and the shielding can are both insulating materials.

Further, the endoscopic sheath, the first baffle, and the second baffle are concentric circles; the first working baffle plate, the second working baffle plate, the third working baffle plate, and the first fixing device are coaxial.

Another purpose of the present invention is to provide a multifunctional compound light penetration enhanced imaging method, comprising the following: the color of the transparent object is determined by the transmitted color light, so what color light passes through, what color is presented; in the white light spectrum, the principle solution is to add illumination light component of a certain wavelength, and depending on the different colors of the translucent substance (such as the fluid mixed with the blood) that blocks the sight, the components of light of different colors are added to achieve enhanced imaging.

When the bleeding at the tissue to be measured is light and the mixed fluid has high transparency, when performing white light projection, the primary color light source collects scattered light into parallel light via the second lens and forms composite white light via the second light combining device, and converges the same into the optical fibre via a coupling output device; the optical fibre transmits the same to the LED lamp; the LED lamp presents the white light and irradiates the same into an interstitial fluid to obtain an image under white light illumination conditions;

When there is much bleeding at the tissue to be tested, the mixed fluid appears red, and when performing red light projection, the red light source collects scattered light into parallel light through the first lens and combines the red light with the white light through the second light combining device, and converges the same into the optical fibre by a coupling output device; the optical fibre transmits the same to the LED lamp; the LED lamp presents the red light and irradiates the same into the interstitial fluid to obtain the image under red light illumination conditions such that the sight in the blood becomes clearer, and the enhanced imaging is realized.

The advantages and positive effects of the present invention when combined with all the above technical solutions are as follows:

the structural design of the present invention is reasonable. Through the cooperation of the first work, the second working baffle plate, and the third working baffle plate, the size of the working baffle plate is switched such that it is adapted to different surgeries. When the system shrinks to the minimum, the opening size of the wound is only 1/3 of that when the system is fully opened, which is suitable for a double-channel spinal endoscopic surgery. When the system is expanded to the maximum, it is suitable for transforaminal endoscopic surgery, and is suitable for multiple surgical modes. By adding a special red light component on the basis of the white light to form compound light illumination and increase the system transmittivity, the background penetration is realized.

The present invention achieves background penetration by adding a special red light component on the basis of the white light to form a compound light illumination and increase the system transmittance; the present invention enhances the illumination, and by providing the first flushing and sucking channel, saline suction under surgery is accomplished, thereby ensuring the clarity of the camera lens in the fluid.

BRIEF DESCRIPTION OF DRAWINGS S

DETAILED DESCRIPTION OF THE EMBODIMENTS

Figure 1:
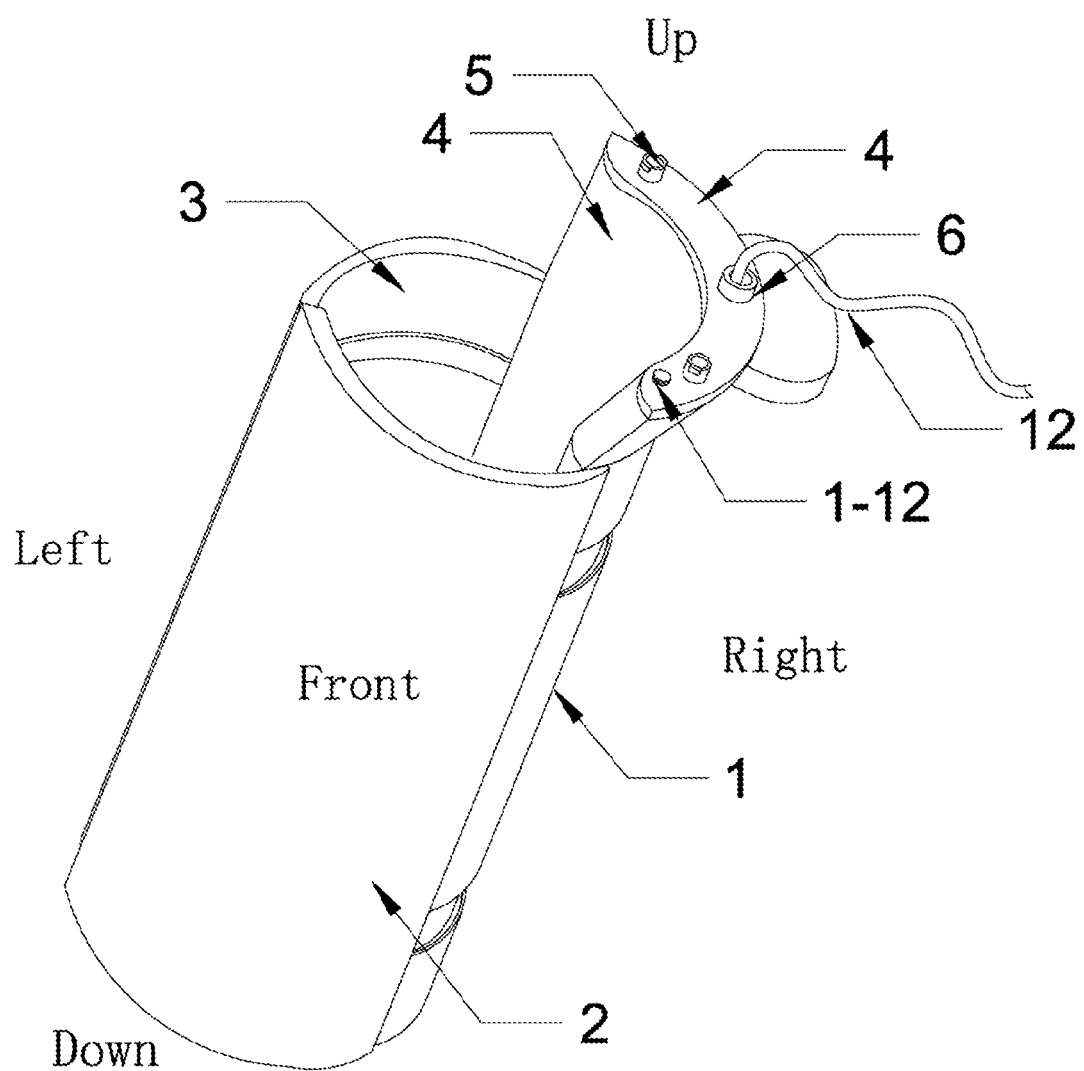
FIG. 1 is a schematic view of a structure of a multifunctional compound light penetration enhanced imaging system provided by an embodiment of the present invention.

In order to make the objects, technical solutions, and advantages of the present invention more apparent, a more particular description of the present invention will be rendered by reference to the embodiments. It should be understood that the particular embodiments described herein are illustrative only and are not limiting.

In view of the problems existing in the prior art, the present invention provides a multifunctional compound light penetration enhanced imaging system. The present invention will be described in detail below with reference to the accompanying drawings.

As shown in FIGS. 1-5, the present invention comprises a first working baffle plate, a second working baffle plate, a third working baffle plate, a first fixing device, a water receiving valve 5, an endoscope fixing device, an outer cylinder 7, a protecting window 8, a second fixing device, a compound illuminating device, a camera device, and a connecting wire 12. The first working baffle plate, the second working baffle plate, the third working baffle plate, and the first fixing device are coaxial.

The first working baffle plate is composed of an endoscopic sheath 1, an endoscopic channel 1-1, a flushing and sucking channel 1-2, a first sliding groove 1-3, a first limiting plate 1-4, a first extension channel 1-5, a first groove 1-6, a first through-hole 1-7, a second groove 1-8, a handle 1-9, a rotating shaft 1-10, a gear 1-11, and a knob 1-12.

The endoscopic sheath 1 is composed of an upper part and a lower part; the lower part of the endoscopic sheath 1 is a semi-arc shape that is symmetric up and below and the cross section is crescent-shaped; the lower end of the upper part of the endoscopic sheath 1 coincides with the lower part thereof, and the outer diameter of the upper end is 1 time of the outer diameter of the lower end, and the radians of the outer-side arc are 130 degrees; the outer wall of the working baffle plate is selected to be arc-shaped so as to facilitate the entry of the system into a human body and avoid scratching which causes secondary injury; the first working baffle plate is selected to be semiarc of 130 degrees;

when the system shrinks to the minimum, the opening size of the wound is only 1/3 of that when the system is fully open, which is suitable for double-channel spinal endoscopic surgery; when the system is expanded to its maximum, it is suitable for a transforaminal endoscopic surgery.

A through endoscopic channel 1-1 is provided in the center of the upper end face and lower end face of the endoscope sheath 1, and arc-shaped flushing and sucking channels 1-2 are symmetrically provided on the left and right with the endoscopic channel 1-1 as the center. A first groove 1-6 is provided at the outer end of the contact position of the upper part and lower part of the endoscopic sheath 1, a second groove 1-8 is provided at the front end of the first groove 1-6 to the rear, a first through-hole 1-7 is provided at the upper end and lower end of the second groove 1-8, the upper end of the first through-hole 1-7 is flush with the upper end face of the endoscopic sheath 1, a rotating shaft 1-10 is inserted into the first through-hole 1-7, and a gear 1-11 is fixedly connected to the rotating shaft 1-10 in the second groove 1-8; the height of the outer side of the gear 1-11 is between the first groove 1-6 and the outer side of the lower part of endoscopic sheath 1; the knob 1-12 is fixedly connected to the upper end of the rotating shaft 1-10 penetrating out of the first through-hole 1-7, and the rotation of the second working baffle plate is controlled by rotating the knob 1-12 so as to adjust the size of the channel.

The upper side and lower side of the outer end of the endoscopic sheath 1 are symmetrically provided with a first sliding groove 1-3 which is opened outwards, the longitudinal section of the first sliding groove 1-3 is T-shaped, the right rear end face of the endoscopic sheath 1 is taken as a starting point, and it rotates clockwise (see FIG. 2) around the center of a circle for 128 degrees to reach an ending point; the upper end and lower end of the first sliding groove 1-3 are symmetrically provided with first extension channels 1-5, and the width of the left front end of the first sliding groove 1-3 is less than the width of the first extension plate 2-4 so as to avoid the first baffle plate 2 from separating from the endoscopic sheath 1 when rotating clockwise; the right rear end face of the endoscopic sheath 1 is taken as the starting point, and the first sliding groove 1-3, which rotates 5 degrees clockwise (see FIG. 2) around the center of a circle to reach the ending point, is fixedly connected with the first limiting plate 1-4 inside, and the outer side of the first limiting plate 1-4 is flush with the outer side of the endoscopic sheath 1.

On the one hand, it ensures that the edge of the outer side is smooth, avoiding scratches that causes secondary injury; on the other hand, it ensures that the rotation direction of the second working baffle plate is fixed, and the second working baffle plate can only rotate out clockwise (see FIG. 2), and when the second working baffle plate rotates back, one side of the first limiting plate 1-4 limits, and the other side of the first limiting plate 1-4 limits the third working baffle plate.

The outer side of the first working baffle plate is clamped with a second working baffle plate, and the second working baffle plate is composed of a first baffle plate 2, a first opening groove 2-1, a first sliding block 2-2, a second sliding groove 2-3, a first extension plate 2-4, a limiting column 2-5, a second opening groove 2-6, and a rack 2-7; the first baffle plate 2 is a long plate with a circular arc shape and the inner diameter thereof is the same as the outer diameter of the endoscopic sheath 1; the inner side of the first baffle plate 2 takes the left rear end face thereof as the starting point, and it rotates around the center of the circle counterclockwise (see FIG. 2) for 125 degrees to reach the ending point where it is fixedly connected with the first sliding block 2-2 with a T-shaped longitudinal section; the first sliding block 2-2 is vertically symmetric and a first extension plate 2-4 is fixedly connected symmetrically at the upper end and lower end of the left rear side of the first sliding block 2-2; the first sliding block 2-2 is adapted to the first sliding groove 1-3 and is clamped in the first sliding groove 1-3; the first extension plate 2-4 is adapted to the first extension channel 1-5 and is clamped in the first extension channel 1-5 such that it is convenient for the first sliding block 2-2 to drive the first baffle plate 2 to slide left and right in the first sliding groove 1-3, and it prevents the first baffle plate 2, when rotating clockwise (see FIG. 2), from rotating out of the first sliding groove 1-3 and derailing from the endoscopic sheath 1. The first baffle plate 2 takes the left rear end face thereof as the starting point, and rotates counterclockwise (see FIG. 2) around the center of a circle by 120 degrees to an ending point; a first opening groove 2-1 is provided on the inner side of the first baffle plate 2; the upper end and lower end of the left rear side first opening groove 2-1 are both fixedly connected with a limiting column 2-5; the outer side of the first sliding block 2-2 is provided with a second sliding groove 2-3, and the second sliding groove 2-3 is in communication with the first opening groove 2-1; the first sliding block 2-2 takes the left rear end face thereof as the starting point, and rotates 5 degrees counterclockwise (see FIG. 2) around the center of the circle to the ending point where a second opening groove 2-6 is provided.

Figure 2:
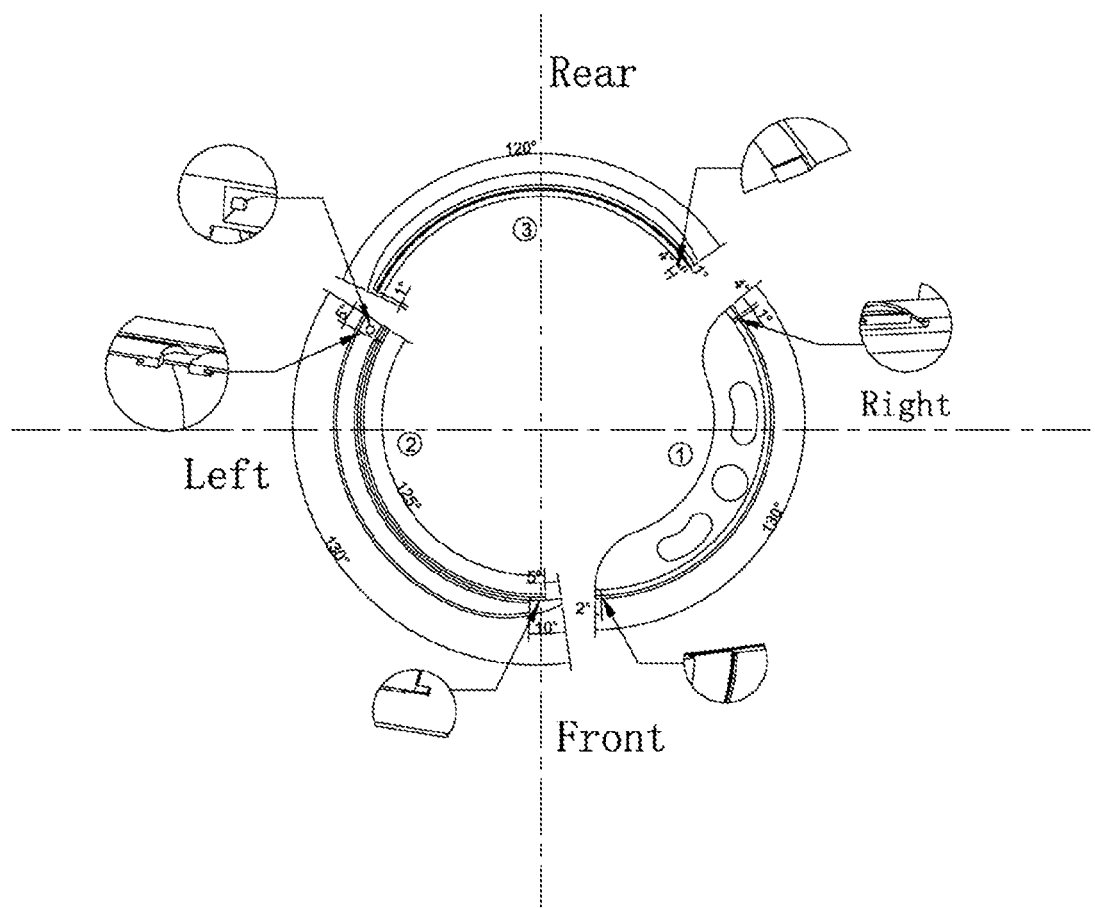
FIG. 2 is a schematic view of a working baffle plate provided by an embodiment of the present invention.
Figure 3:
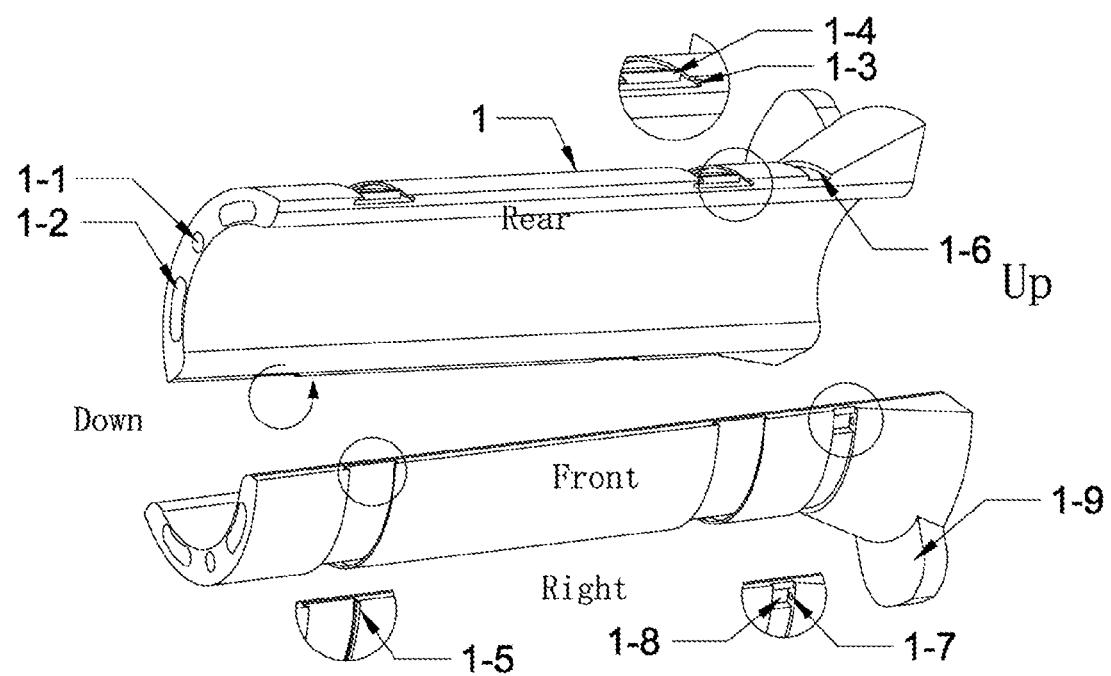
FIG. 3 is a schematic view of the structure of a first working baffle plate provided by an embodiment of the present invention.
Figure 4:
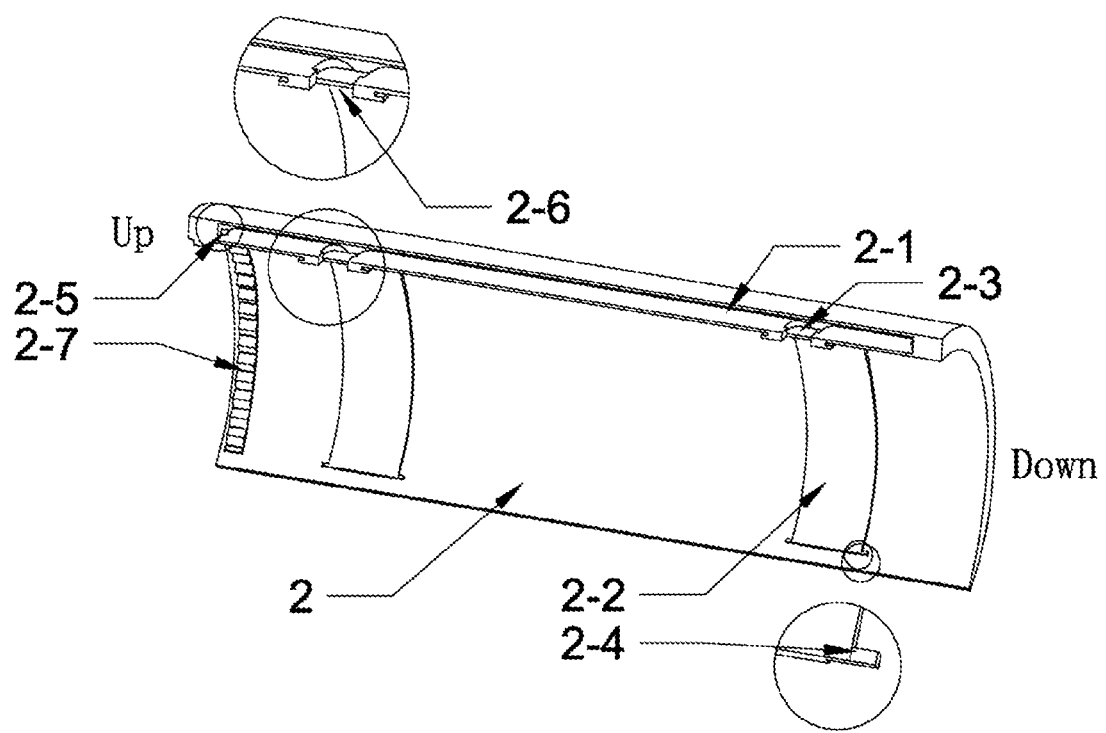
FIG. 4 is a schematic view of the structure of a second working baffle plate provided by an embodiment of the present invention.
Figure 5:
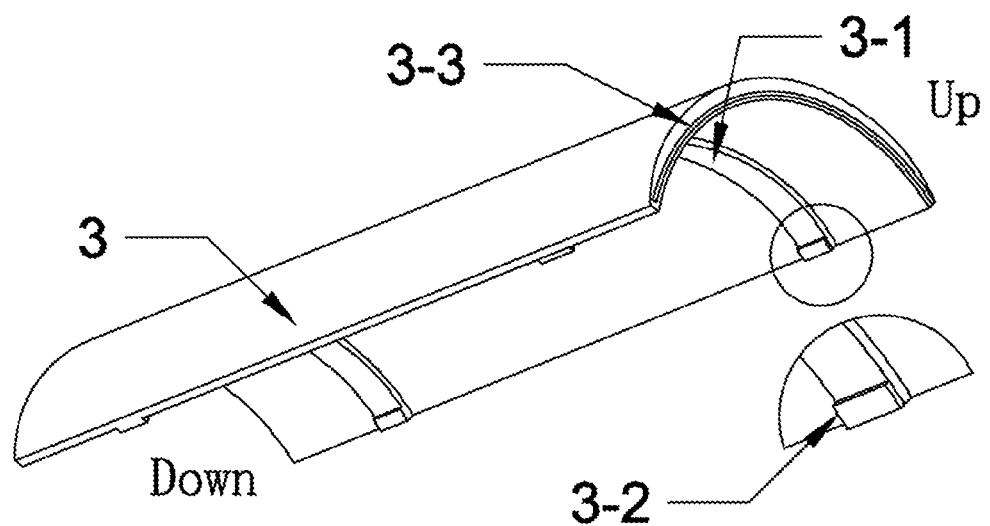
FIG. 5 is a schematic view of the structure of a third working baffle plate provided by an embodiment of the present invention.
Figure 6:
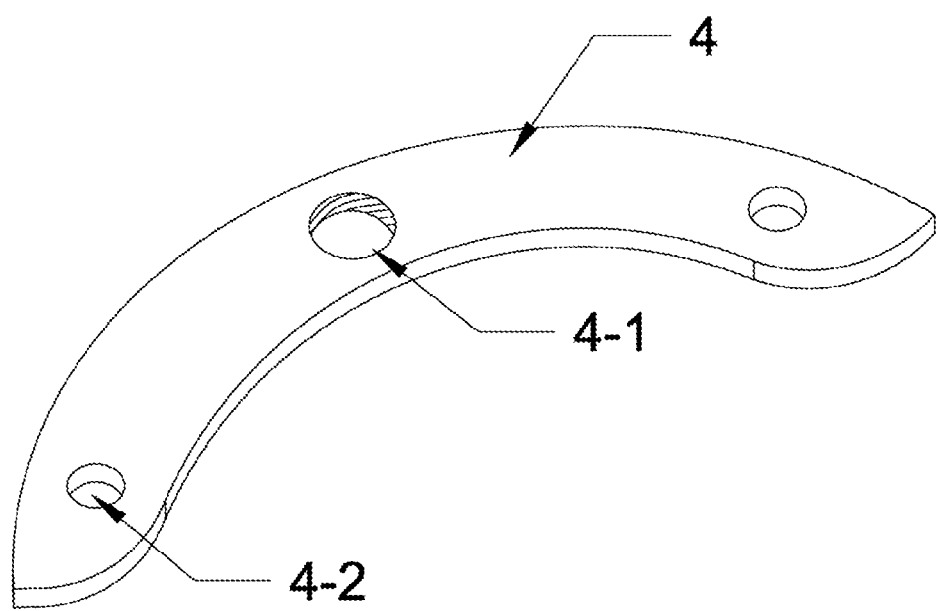
FIG. 6 is a schematic view of the structure of a first fixing device provided by an embodiment of the present invention.
Figure 7:
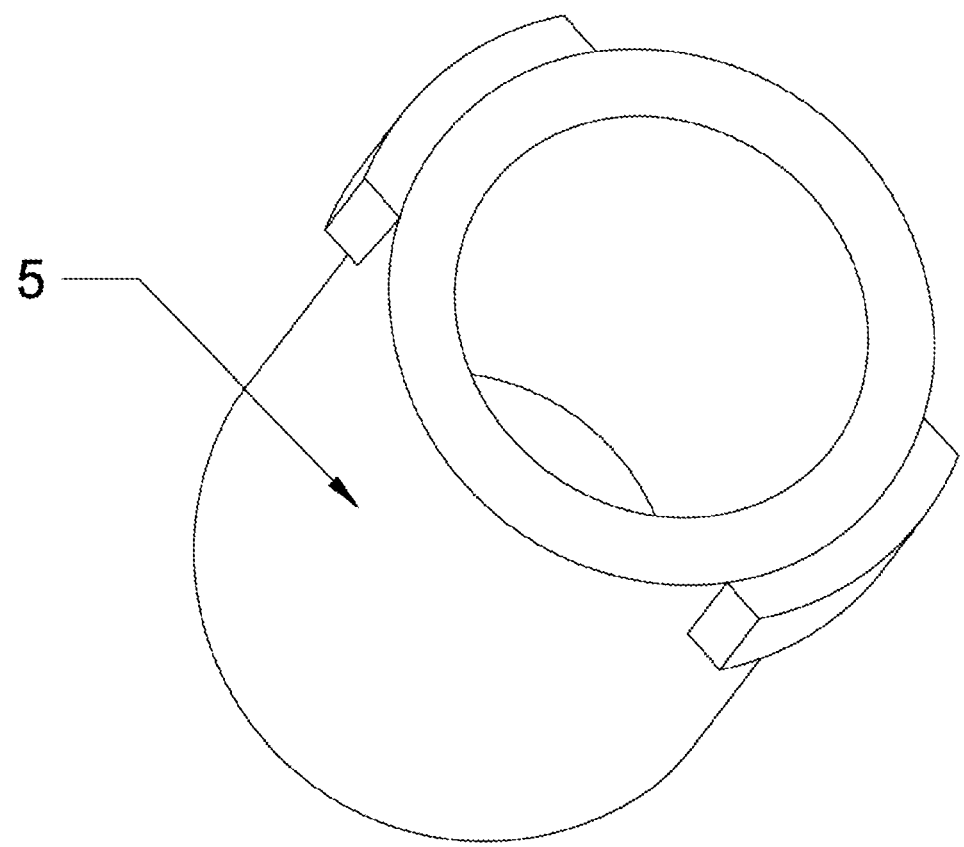
FIG. 7 is a schematic view of the structure of a universal water receiving valve provided by an embodiment of the present invention.
Figure 8:
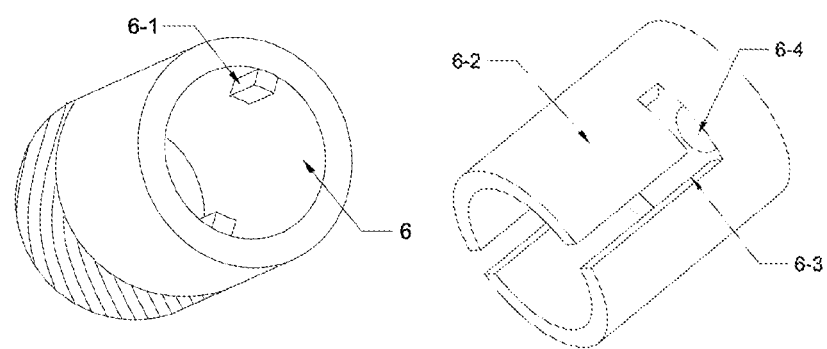
FIG. 8 is a schematic view of the structure of an endoscope fixing device provided by an embodiment of the present invention.
Figure 9:
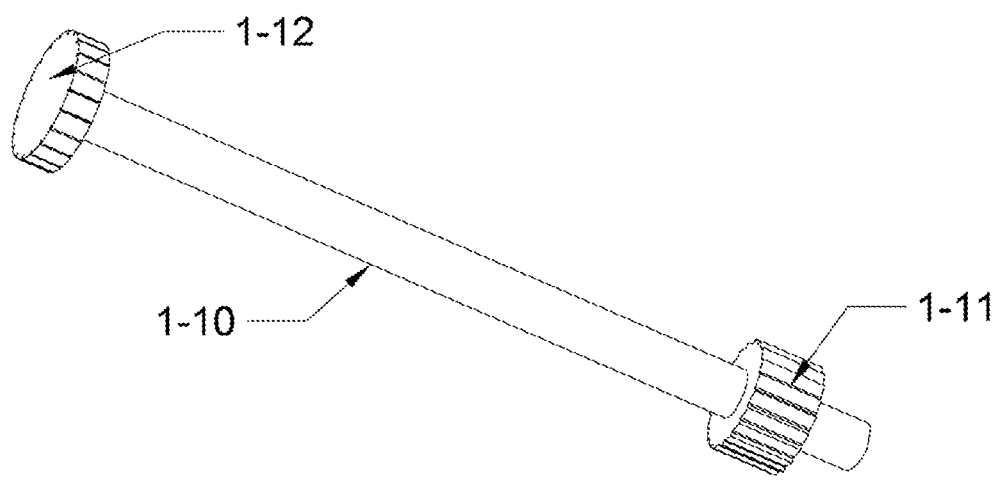
FIG. 9 is a schematic view of a gear position structure provided by an embodiment of the present invention.
Figure 10:
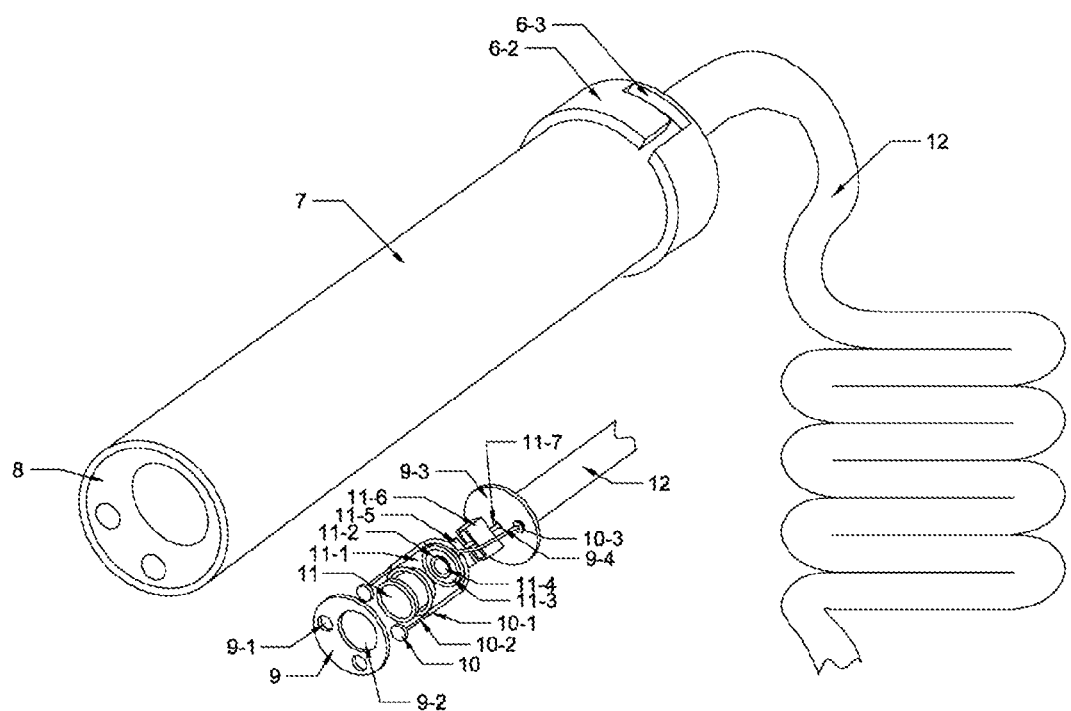
FIG. 10 is a schematic view of the structure of an endoscope provided by an embodiment of the present invention.
Figure 11:
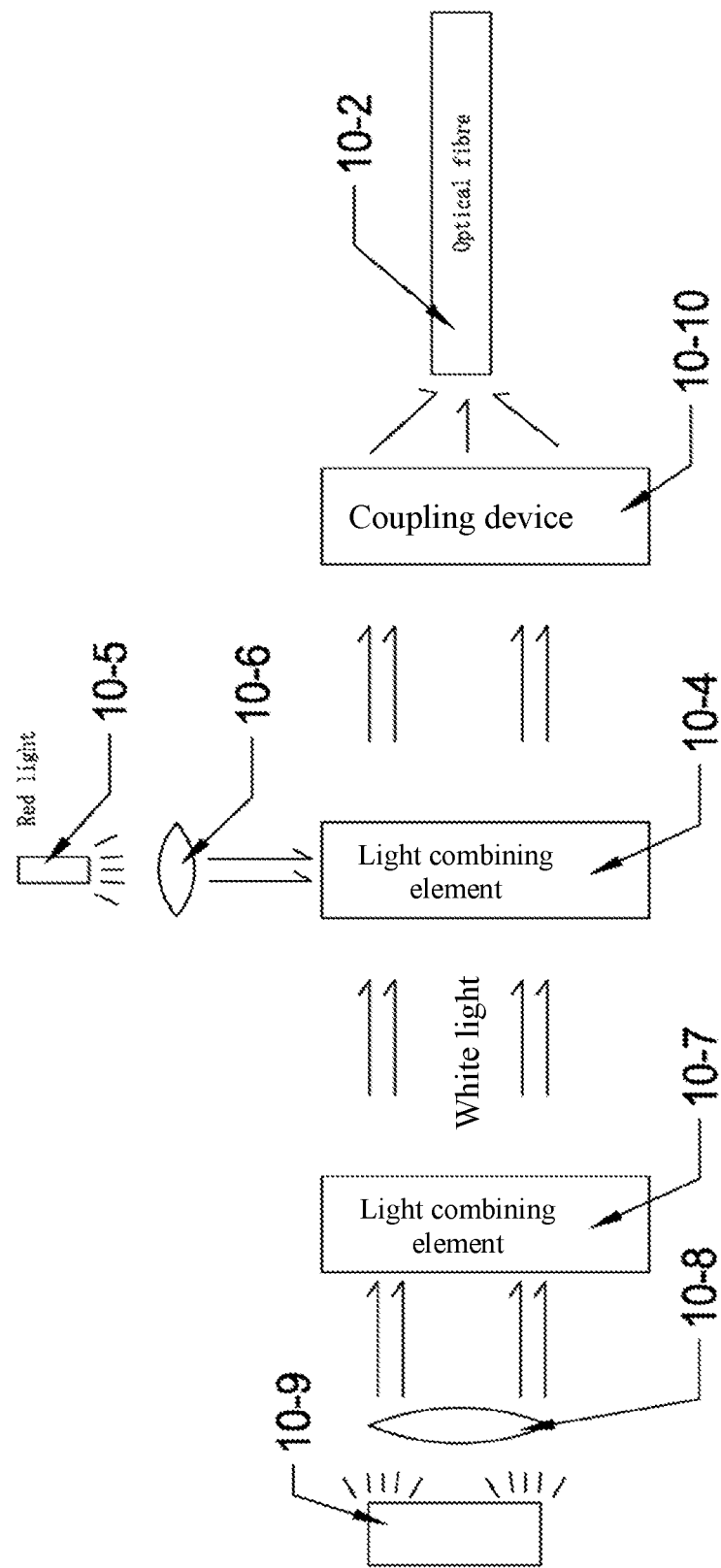
FIG. 11 is a schematic view of a light path of an illuminating device provided by an embodiment of the present invention.
Figure 12:
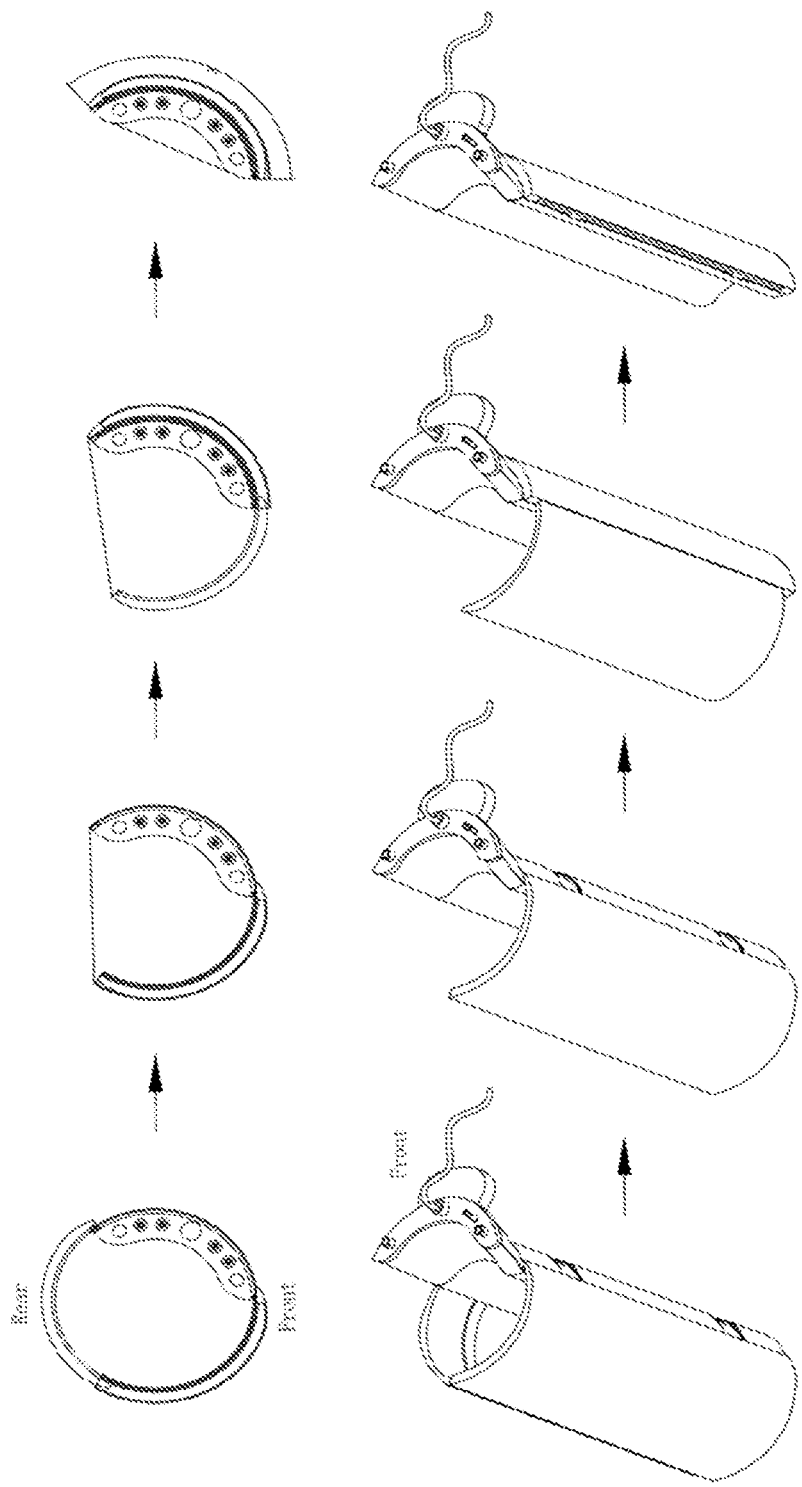
FIG. 12 is a schematic view of an illustrative structure provided by an embodiment of the present invention.

The inner side of the second working baffle plate is clamped and connected with a third working baffle plate; the inner side of the upper end of the first baffle plate 2 is fixedly connected with a rack 2-7 and the rack meshes with a gear 1-11; the third working baffle plate is composed of a second baffle plate 3, a second sliding block 3-1, a second limiting plate 3-2, and a limiting groove 3-3; the shape of the second baffle plate 3 is similar to that of the first opening groove 2-1 and the second baffle plate 3 is inserted into the first opening groove 2-1; the upper end and lower end of the inner side of the second baffle plate 3 are symmetrically fixedly connected with the second sliding block 3-1 and are clamped in the second sliding groove 2-3; the second sliding block 3-1 takes the right rear end face of the second baffle plate 3 as the starting point, and rotates 5 degrees counterclockwise (see FIG. 2) around the center of a circle to an ending point where a second limiting block is fixedly connected to the inner side; the second limiting block is adapted to the size and shape of the second opening groove 2-6 and can be clamped in the second opening groove 2-6; the second baffle plate 3 takes the left rear end face thereof as the starting point, and rotates 1 degree clockwise (see FIG. 2) around the center of the circle to the ending point, the upper end and lower end thereof being provided with limiting grooves 3-3; the limiting column 2-5 is clamped in the limiting groove 3-3; the second opening groove 2-6 cooperates with the second limiting block to ensure that the second baffle plate 3 fully rotates back into the first opening groove 2-1 when rotating back; the cooperation of the limiting column 2-5 and the limiting groove 3-3 prevents the second baffle plate 3 from rotating out of the second sliding groove 2-3 and derailing from the first baffle plate 2 when the second baffle plate 3 rotates clockwise (see FIG. 2).

The first fixing device is composed of a first fixing plate 4, an internal thread hole 4-1, and a second through-hole 4-2. The first fixing plate 4 has the same shape and size as those of the upper end of the endoscopic sheath 1 and is fixedly connected to the upper end of the endoscopic sheath 1. An internal thread hole 4-1 is provided in the middle of the first fixing plate 4, and second through-holes 4-2 are symmetrically provided on the left side and right side of the first fixing plate 4. The internal thread hole 4-1 corresponds to the endoscopic channel 1-11-1 and the second channel is located directly above the second flushing and sucking channel 1-2. A general medical water receiving valve 5 is fixedly connected in the second through-hole 4-2, and the internal thread hole 4-1 is internally threaded and connected to the endoscope fixing device.

The endoscope fixing device is composed of a lower fixing cylinder 6, a clamping block 6-1, an upper fixing cylinder 6-2, an L-shaped clamping groove 6-3, and a fifth through-hole 6-4. The lower fixing cylinder 6 is a cylinder provided with an external thread line at the outer end of the lower side and is threadedly connected in the internal thread hole 4-1, the clamping block 6-1 is fixed symmetrically on the front side and rear side of the upper inner end of the lower fixing cylinder 6, the outer diameter of the upper fixing cylinder 6-2 is the same as the inner diameter of the lower fixing cylinder 6, and the fifth through-hole 6-4 is provided in the middle of the upper end; the L-shaped clamping groove 6-3 is symmetrically arranged at the center of the front end and rear end of the lower side of the upper fixing cylinder 6-2, and the clamping block 6-1 is clamped in the L-shaped clamping groove 6-3 to facilitate the connection of the endoscope with the working baffle plate; the upper fixing cylinder 6-2 is fixedly connected to the upper end of the outer cylinder 7, and a protecting window 8 is fixedly connected to the inner side of the lower end of the outer cylinder 7.

The second fixing device is composed of a second fixing plate 9, a third through-hole 9-1, a fourth through-hole 9-2, a third fixing plate 9-3, and a first routing hole 9-4; the second fixing plate 9 and the third fixing plate 9-3 are both circular plates and have the same outer diameter as the inner diameter of the outer cylinder 7; the second fixing plate 9 is fixedly connected to the outer cylinder 7 at the upper end of the protecting window 8; the front end of the second fixing plate 9 is provided with the fourth through-hole 9-2; the rear end is symmetrically, on the left and right, provided with two third through-holes 9-1; the middle of the third fixing device is provided with the first routing hole 9-4.

The camera device is composed of a lens 11, an insulating sleeve 11-1, an image sensor 11-2, a receiving plate 11-3, a second routing hole 11-4, a PCB board 11-5, a shielding can 11-6, and a signal cable 11-7. The lower end of the camera lens 11 is clamped in the fourth through-hole 9-2 and the upper end of the camera lens 11 is electrically connected to the image sensor 11-2; the image sensor 11-2 is fixedly connected to the receiving plate 11-3 and is electrically connected to the PCB board 11-5, and the outer end of the image sensor 11-2 is sleeved with the shielding can 11-6; the lower end of the PCB board 11-5 is electrically connected with a signal cable 11-7, and the upper end of the signal cable 11-7 is inserted into the connecting wire 12 by passing through the first routing hole 9-4.

An insulating sleeve 11-1 is sleeved on the outer side of the intermediate assembly of the second fixed plate 9 and the third fixed plate 9-3; the compound illuminating device is composed of an LED lamp 10, an L-shaped line tube 10-1, an optical fibre 10-2, a control box 10-3, a first light combining element 10-4, a red light source 10-5, a first lens 10-6, a second light combining device 10-7, a second lens 10-8, a primary color light source 10-9, and a coupling device 10-10; two LED lamps 10 are provided to be respectively clamped in the third through-hole 9-1, and the upper end of the LED lamp 10 is electrically connected to the optical fibre 10-2; the optical fibre 10-2 passes through the L-shaped line tube 10-1 at the left end and right end of the insulating sleeve 11-1 to be electrically connected to the control box 10-3; a first light combining element 10-4, a red light source 10-5, a first lens 10-6, a second light combining device 10-7, a second lens 10-8, a primary color light source 10-9, and a coupling device 10-10 are provided in the control box 10-3; the intensities of the primary color light source 10-9 and the red light source 10-5 are adjustable; the right side of the primary color light source 10-9 is successively provided with the second lens 10-8, the second light combining element, the first light combining element 10-4, and the coupling device 10-10;

the upper end of the first light combining element 10-4 is successively provided with a first lens 10-6 and a red light source 10-5, the first light combining element 10-4 and the second light combining element are both dichroscopes, and an optical fibre 10-2 is connected to the right side of the coupling device 10-10; the color of the transparent object is determined by the transmitted color light, and what color light passes through results in what color being presented; the color of an opaque object is determined by the color light it reflects.

When white light is required, the primary-color light source 10-9 collects the scattered light into parallel light through the second lens 10-8 and forms the composite white light through the second light combining device 10-7, and converges the same into the optical fibre 10-2 by the coupling output device; the optical fibre 10-2 transmits the same to the LED lamp 10; the LED lamp 10 presents white light and irradiates the same into the interstitial fluid to obtain an image under white light illuminating conditions; when red light is required, the red light is added on the basis of the white light; the red light source 10-5 collects the scattered light into parallel light through the first lens 10-6 and combines the red light with the white light through the second light combining device 10-7, and converges the same into the optical fibre 10-2 by a coupling output device; the optical fibre 10-2 transmits the same to the LED lamp 10; the LED lamp 10 presents the red light and irradiates the same into the interstitial fluid to obtain an image under the red light illuminating conditions; it is different from the narrow-band imaging technique as the narrow-band imaging technique is to add a narrow-band rotary optical filter at the rear end of the white light source so as to generate the narrow-band light and perform illuminated imaging on an examined part. That is, at a certain moment, a certain monochromatic light illuminates the tissue, and at the next moment, another monochromatic light illuminates the tissue, so as to obtain images under illumination conditions at different moments, and then the color enhancement is realized through algorithmic synthesis. It uses the specificity of the tissue to be imaged for the emitted light to form an enhanced image. When the narrow-band light is imaged, after passing through the optical filter, most of the energy is absorbed by the optical filter, and only little energy transmits through the optical filter. Therefore, on the one hand, this imaging mode will lead to the loss of the wide spectrum light, resulting in energy waste; on the other hand, the energy absorbed by the optical filter will be converted into heat, causing an additional heat treatment burden. The principle scheme is to use the different light transmitted by the object to different wavelengths to form an enhanced image.

Figure 13:
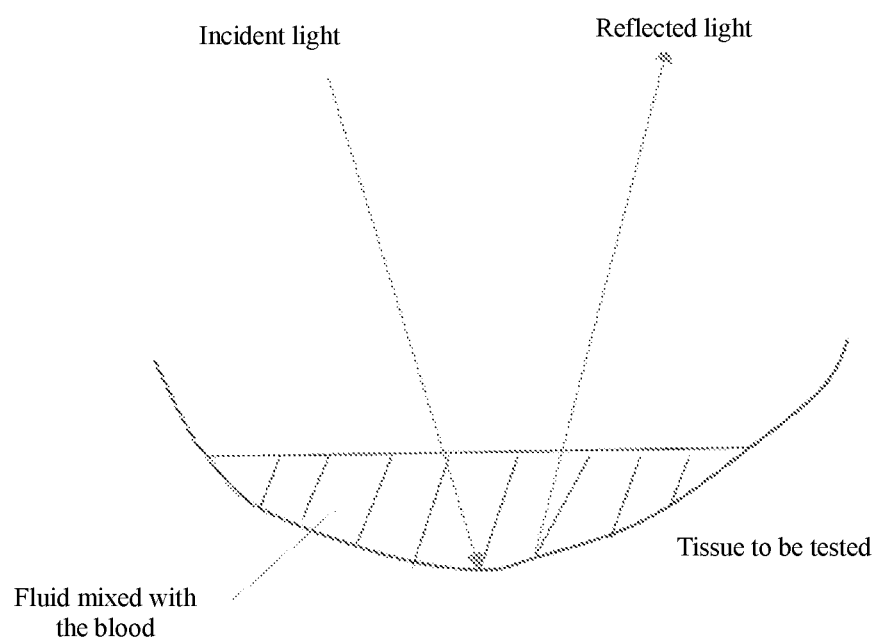
FIG. 13 is a schematic view of an imaging mode provided by an embodiment of the present invention.
Figure 14:
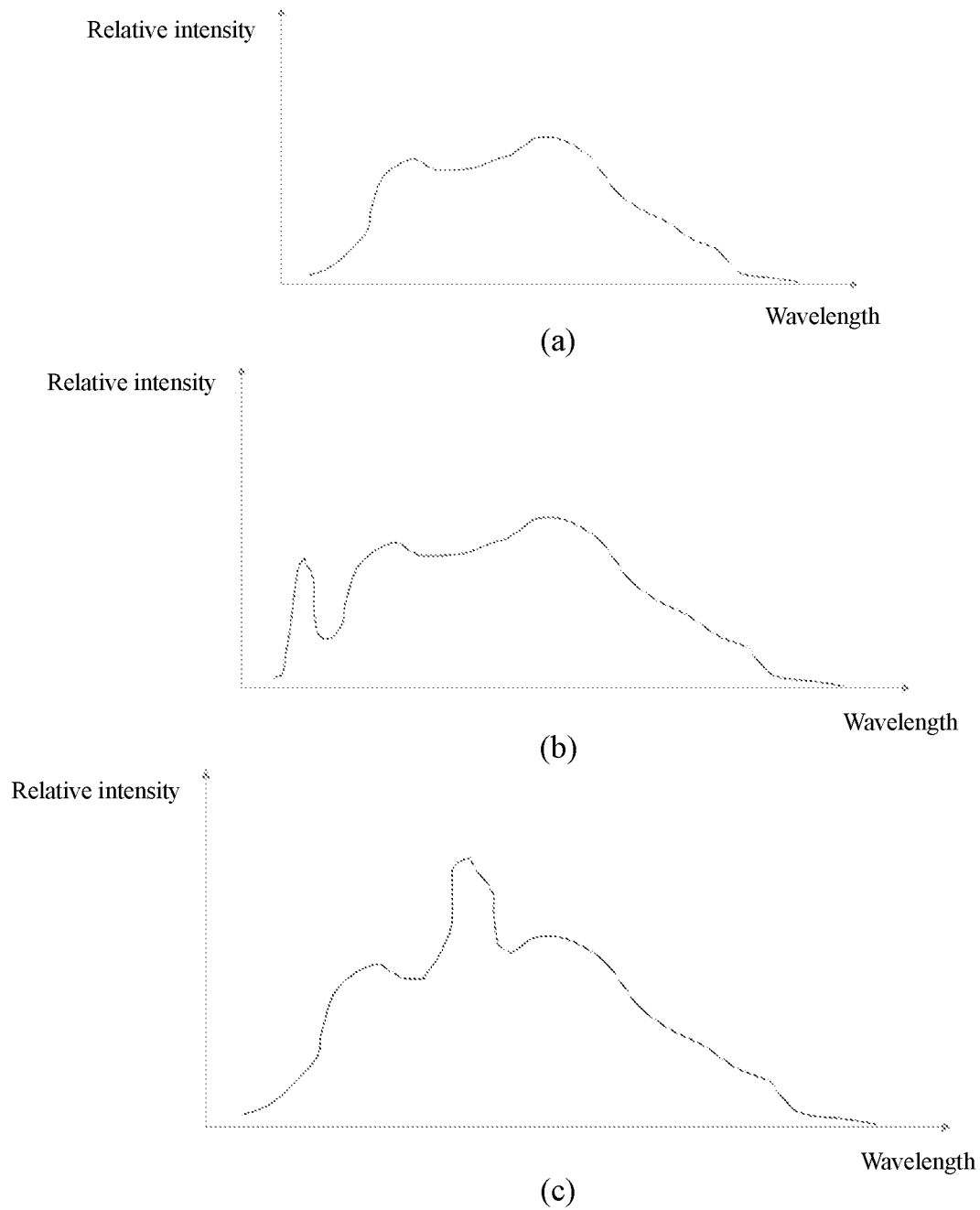
FIG. 14 is a schematic view illustrating a verification effect provided by an embodiment of the present invention.
Figure 15:
FIG. 15 is a graph comparing the same object illuminated with white light (FIG. 15 (*a*)) and imaged with the addition of red light component (FIG. 15 (*b*)) in the same experimental environment provided by an embodiment of the present invention.
Figure 15:

As shown in FIG. 13, bleeding occurs at the tissue to be tested. Although flushing is carried out with the saline, there is residual blood, blocking the sight. The fluid mixed with the blood appears red, with the absorption of red light being minimum, and the absorption of light of other colors such as blue light being maximum; therefore, the present invention adds a red light source 10-5 to the illuminating light at this moment; the red light component penetrates through the fluid mixed with the blood, irradiates the tissue, and is then reflected, and penetrates through the fluid mixed with the blood again, and performs imaging via a camera device, with the loss of the added red light component being minimum, thereby achieving the enhanced penetration of the fluid and achieving a good imaging effect. As shown in FIG. 14, FIG. 14 (*a*) is a common white light illumination spectrum, and in the white light spectrum an illumination light component of a certain wavelength is added, as shown in FIG. 14 (*b*) and FIG. 14 (*c*), an enhancement spectrum component marked by a red line, and depending on the different colors of the translucent substance (such as the fluid mixed with the blood) that blocks the sight, the components of light of different colors are added to achieve enhanced imaging. In the endoscopic imaging of the present invention, under the same experimental environment, the contrast diagram of the same object with white light illumination (FIG. 15 (*a*)) and the imaging after adding the red light component (FIG. 15 (*b*)) is shown in FIG. 15. The nut in a small beaker filled with red ink is hardly visible under white light, and the nut can be seen after adding red light illumination component according to the present invention to enhance the imaging.

As provided in the embodiments of the present invention, the insulating sleeve 11-1 and the shielding can 11-6 are both insulating materials, which play a protective role on the elements and prevent the signal interference of the electronic endoscope caused by the external induced current from affecting the image quality.

According to an embodiment of the present invention, the endoscopic sheath 1, the first baffle plate 2, and the second baffle plate 3 are concentric circles so as to facilitate collecting and putting away.

The specific working principle of the present invention is as follows:

the present invention achieves background penetration by adding a special red light component on the basis of the white light to form a compound light illumination and increase the system transmittivity; during a surgery, when the bleeding at the tissue to be tested blocks the sight, the fluid mixed with the blood appears red, with the minimum absorption for the red light and the maximum absorption for other colors such as blue light. At this moment, the red light component penetrates through the fluid mixed with the blood, irradiates the tissue, and then is reflected, and penetrates through the fluid mixed with the blood again, and undergoes imaging by the camera device, with the minimum loss of the added red light component, so as to achieve the enhanced penetration of the fluid and achieve a good imaging effect without sacrificing the imaging speed and thus simplifying the image processing flow; it can realize the enhanced image effect without changing the current machine structure but only changing the illuminating light source. In addition, the inner wall and outer wall of the first working baffle plate, the second working baffle plate, and the third working baffle plate are all arc-shaped, so as to facilitate the device in entering the human body, and avoid scratching which causes secondary injury; a rotating shaft 1-10 is inserted into the first through-hole 1-7, a gear 1-11 is fixedly connected to the rotating shaft 1-10 in the second groove 1-8, and a knob 1-12 fixedly connected to the upper end of the rotating shaft 1-10; an endoscopic sheath 1, a first baffle plate 2, and a second baffle plate 3 can slide against each other therebetween, and the three are coaxial, and the arc size of a combined opening is between 130 degrees and 360 degrees.

The knob 1-12 is turned counterclockwise (see FIG. 2), and the second baffle plate 3 slides into the first opening groove 2-1 counterclockwise (see FIG. 2) via the first sliding block 2-2 fixedly connected to the inner side of the second baffle plate 3; when the first sliding block 2-2 slides into the first sliding groove 1-3 counterclockwise (see FIG. 2), the right rear end of the first sliding block 2-2 is in contact with and connected to the first limiting plate 1-4, and the endoscopic sheath 1 is flush with the outer side of the first baffle plate 2; at the same time, the second baffle plate 3 slides into the first opening groove 2-1 counterclockwise (see FIG. 2), and at this moment, the limiting column 2-5 is clamped and connected to the left rear end of the limiting groove 3-3, and the second limiting plate 3-2 at the rear end of the second baffle plate 3 is clamped and connected to the inside of the second opening groove 2-6 for easy turning out, and the left rear end of the second baffle plate 3 is flush with the left rear end of the first baffle plate 2; at this time, the device shrinks to the minimum, and the opening size of wound is only 1/3 of that when the system is fully opened, which is suitable for a double-channel spinal endoscopic surgery. The knob 1-12 is turned clockwise (see FIG. 2), and the second baffle plate 3 slides out of the first opening groove 2-1 clockwise (see FIG. 2) through the first sliding block 2-2 fixedly connected to the inner side of the second baffle plate 3; when the first sliding block 2-2 slides out of the first sliding groove 1-3 counterclockwise (see FIG. 2), the first extension plate 2-4 fixedly connected to the right rear end of the first sliding block 2-2 is clamped at the left front end of the first extension channel 1-5 to limit the second baffle plate 3 so as to prevent the first baffle plate 2 from derailing from the endoscopic sheath 1; at the same time, the second baffle plate 3 slides out of the first opening groove 2-1 clockwise (see FIG. 2), and at this moment, the limiting column 2-5 is clamped at the right front end of the limiting groove 3-3 to prevent the second baffle plate 3 from derailing from the first baffle plate 2, and the front end of the second limiting plate 3-2 at the rear end of the second baffle plate 3 is in contact with and connected to the rear end of the first limiting plate 1-4; the device is at the time expanded to the maximum size suitable for the transforaminal endoscopic surgery and can be adjusted as needed when the surgery requires the opening size outside of the above two.

The above are only preferred embodiments of the present invention, and the scope of the present invention is not limited to this. Any modifications, equivalent replacements, and improvements made within the spirit and principle of the present invention by any person skilled in the art within the technical scope disclosed by the present invention shall be covered within the protection scope of the present invention.

What is claimed is:

1. A multifunctional compound light penetration enhanced imaging system, wherein the multifunctional compound light penetration enhanced imaging system is provided with a first working baffle plate, a second working baffle plate, and a third working baffle plate; the second working baffle plate is clamped on an outer side of the first working baffle plate; the third working baffle plate is slidably inserted in an inner cavity of the second working baffle plate;

the first working baffle plate is composed of an endoscopic sheath, an endoscopic channel, a flushing and sucking channel, a first sliding groove, a first limiting plate, a first extension channel, a first groove, a first through-hole, a second groove, a handle, a rotating shaft, a gear, and a knob;

the second working baffle plate is composed of a first baffle plate, a first opening groove, a first sliding block, a second sliding groove, a first extension plate, a limiting column, a second opening groove, and a rack;

the third working baffle plate is composed of a second baffle, a second sliding block, a second limiting plate, and a limiting groove;

an inner wall and an outer wall of the first working baffle plate, the second working baffle plate, and the third working baffle plate are all circular arc-shaped; the rotating shaft is inserted into the first through-hole, the gear is fixedly connected to the rotating shaft in the second groove, and the knob is fixedly connected to an upper end of the rotating shaft; the endoscopic sheath, the first baffle plate, and the second baffle plate can slide against each other therebetween and are coaxial, and an arc size of a combined opening is between 130 degrees and 360 degrees;

the endoscopic sheath is composed of an upper part and a lower part; the lower part of the endoscopic sheath is a semi-arc shape symmetrical up and down and has a crescent-shaped cross section; a lower end of the upper part of the endoscopic sheath coincides with the lower part of the endoscopic sheath, and an outer diameter of the upper end of the upper part of the endoscopic sheath is 1 times the outer diameter of the lower end of the upper part of the endoscopic sheath, and an arc radian of the outer side of the upper part of the endoscopic sheath is 130 degrees; a through endoscopic channel is provided at a center of an upper end face and a lower end face of the endoscopic sheath, and the arc-shaped flushing and sucking channel is provided symmetrically left and right with the endoscopic channel as the center; an outer end of a contact position of the upper part and the lower part of the endoscopic sheath is provided with the first groove, a front end of the first groove is provided rearward with the second groove, and the upper end and lower end of the second groove are provided with the a first through-hole;

the upper end of the first through-hole is flush with the upper end face of the endoscopic sheath, the rotating shaft is inserted into the first through-hole and the gear is fixedly connected to the rotating shaft in the second groove, a height of an outside of the gear is between the first groove and the outer side of the lower part of the endoscopic sheath, and the knob is fixedly connected to the upper end of the rotating shaft penetrating out of the first through-hole; the upper side and lower side of the outer end of the endoscopic sheath are symmetrically provided with the first sliding groove opening outwards; a longitudinal section of the first sliding groove is T-shaped, and the first sliding groove takes a right rear end face of the endoscopic sheath as a starting point and rotates clockwise around the center of a circle to an ending point by 128 degrees, wherein a sequence from the first working baffle plate to the second working baffle plate to the third working baffle plate is clockwise from a perspective of a distal end of an endoscope; a first extension channel is symmetrically provided on the upper end and the lower end of the first sliding groove, wherein the first extension channel takes a right rear end face of the endoscopic sheath as the starting point, and rotates clockwise around the center of a circle by 5 degrees to the ending point where the first limiting plate is fixedly connected in the first sliding groove, and the outer side of the first limiting plate is flush with the outer side of the endoscopic sheath.

2. The multifunctional compound light penetration enhanced imaging system according to claim 1, wherein the first baffle plate is the circular arc-shaped long plate and the inner diameter of the first baffle plate is the same as that of the endoscopic sheath; the inner side of the first baffle plate takes a left rear end face of the inner side of the first baffle plate as the starting point and rotates counterclockwise around the center of a circle by 125 degrees to the ending point where the first sliding block having a T-shaped longitudinal section is fixedly connected; the first sliding block is symmetrical up and down, and the first extension plate is fixedly connected symmetrically at the upper end and lower end of a left rear side of the first sliding block, and the first sliding block is adapted to the first sliding groove and is clamped therein, and the first extension plate is adapted to the first extension channel and is clamped therein; the first baffle plate takes a left rear end face of the first baffle plate as the starting point and rotates counterclockwise around the center of a circle by 120 degrees to the ending point, the first opening groove is provided on the inner side of the first baffle plate, and the upper end and lower end of the first opening groove on a left rear side are both fixedly connected with the limiting column; the second sliding groove is provided on the outer side of the first sliding block, and the second sliding groove is in communication with the first opening groove, and the first sliding block takes a left rear end face of the first sliding block as the starting point and rotates counterclockwise around the center of a circle by 5 degrees to the ending point where a second opening groove is provided; the rack is fixedly connected to the inner side of the upper end of the first baffle plate, and the rack meshes with the gear.

3. The multifunctional compound light penetration enhanced imaging system according to claim 1, wherein the second baffle plate is similar in shape to the first opening groove and the second baffle plate is inserted into the first opening groove;

the second sliding block is fixedly connected to the upper end and lower end of the inner side of the second baffle plate, and the second sliding block is clamped in the second sliding groove; the second sliding block takes a right rear end face of the second baffle plate as the starting point and rotates counterclockwise around the center of a circle by 5 degrees to the ending point where a second limiting block is fixedly connected, and the second limiting block is adapted to a size and shape of the second opening groove and is clamped in the second opening groove;

the second baffle plate takes the left rear end face thereof as the starting point and rotates clockwise around the center of a circle by 1 degree to the ending point where the limiting groove is provided at the upper end and lower end of the ending point, and the limiting column is clamped in the limiting groove.

4. The multifunctional compound light penetration enhanced imaging system according to claim 1, wherein the multifunctional compound light penetration enhanced imaging system is further provided with:

a first fixing device, a second fixing device, a third fixing device, a compound illuminating device, a camera device, and a connecting wire;

wherein the first fixing device is composed of a first fixing plate, an internal thread hole, and a second through-hole;

the second fixing device is composed of a second fixing plate, a third through-hole, a fourth through-hole, a third fixing plate, and a first routing hole;

the first routing hole is provided in a middle of the third fixing device;

the compound illuminating device is composed of an LED lamp, an L-shaped line tube, an optical fibre, a control box, a first light combining element, a red light source, a first lens, a second light combining element, a second lens, a primary color light source, and a coupling device;

the camera device is composed of a camera lens, an insulating sleeve, an image sensor, a receiving plate, a second routing hole, a PCB board, a shielding can, and a signal cable.

5. The multifunctional compound light penetration enhanced imaging system according to claim 4, wherein the first fixing plate has the same shape and size as the upper end of the endoscopic sheath and is fixedly connected to the upper end of the endoscopic sheath;

the internal thread hole is provided in the middle of the first fixing plate, and the second through-holes are symmetrically provided on the left side and right side of the first fixing plate;

the internal thread hole corresponds to the endoscopic channel and a second channel is located directly above a second flushing and sucking channel;

a general medical water receiving valve is fixedly connected in the second through-hole, and an endoscope fixing device is threadedly connected in the internal thread hole; the endoscope fixing device is composed of a lower fixing cylinder, a clamping block, an upper fixing cylinder, an L-shaped clamping groove, and a fifth through-hole;

the lower fixing cylinder is a cylinder provided with an external thread line at the outer end of the lower side, and a thread of the cylinder is connected in the internal thread hole; the clamping block is symmetrically fixedly connected at the front side and rear side of the inner end of the upper part of the lower fixing cylinder; the outer diameter of the upper fixing cylinder is the same as that of the lower fixing cylinder, and the fifth through-hole is provided in the middle of the upper end of the upper fixing cylinder; the L-shaped clamping groove is symmetrically arranged at the center of the front end and rear end of the lower side of the upper fixing cylinder, and the clamping block is clamped in the L-shaped clamping groove; the upper fixing cylinder is fixedly connected to the upper end of an outer cylinder, and a protecting window is fixedly connected to the inner side of the lower end of the outer cylinder.

6. The multifunctional compound light penetration enhanced imaging system according to claim 4, wherein the second fixing plate and the third fixing plate are both circular plates and the outer diameter thereof is the same as an inner diameter of the outer cylinder, the second fixing plate is fixedly connected to the outer cylinder at the upper end of the protecting window, the front end of the second fixing plate is provided with the fourth through-hole, and the rear end of the second fixing plate is symmetrically provided with two third through-holes on the left and right;

the insulating sleeve is sleeved on the outer side of an intermediate assembly of the second fixing plate and the third fixing plate;

the lower end of the camera lens is clamped in the fourth through-hole and the upper end of the camera lens is electrically connected to the image sensor;

the image sensor is fixedly connected to the receiving plate and is electrically connected to the PCB board, and an outer end of the image sensor is sleeved with the shielding can, the lower end of the PCB board is electrically connected to the signal cable, and the upper end of the signal cable is inserted into the connecting wire through the first routing hole;

the two LED lamps are provided and are respectively clamped in the third through-hole and the upper end of the LED lamp is electrically connected with the optical fibre;

the optical fibre passes through the L-shaped line tube at the left end and right end of the insulating sleeve and is electrically connected to the control box;

the control box is provided therein with the first light combining element, the red light source, the first lens, the second light combining element, the second lens, the primary color light source, and the coupling device;

intensities of the primary color light source and the red light source are adjustable; the right side of the primary color light source is successively provided with the second lens, the second light combining element, the first light combining element, and the coupling device;

the upper end of the first light combining element is successively provided with the first lens and the red light source; the first light combining element and the second light combining element are both dichroscopes; the optical fibre is connected to the right side of the coupling device.

7. The multifunctional compound light penetration enhanced imaging system according to claim 6, wherein the insulating sleeve and shielding are both of insulating materials;

the endoscopic sheath, the first baffle, and the second baffle are concentric circles; the first working baffle plate, the second working baffle plate, the third working baffle plate, and the first fixing device are coaxial.

8. A multifunctional compound light penetration enhanced imaging method using the multifunctional compound light penetration enhanced imaging system according to claim 1, wherein the multifunctional compound light penetration enhanced imaging method comprises:

switching the size of the working baffle plate through a cooperation of the first working baffle plate, the second working baffle plate, and the third working baffle plate;

wherein when performing white light projection, the primary color light source collects scattered light into parallel light via the second lens and forms composite white light via the second light combining element, and converges same into the optical fibre via a coupling output device; the optical fibre transmits the same to the LED lamp; the LED lamp presents the white light and irradiates the same into an interstitial fluid to obtain an image under white light illumination conditions;

when performing red light projection, the red light source collects scattered light into parallel light through the first lens and combines the red light with the white light through the second light combining element, and converges the same into the optical fibre by the coupling output device; the optical fibre transmits the same to the LED lamp; the LED lamp presents the red light and irradiates the same into the interstitial fluid to obtain the image under red light illumination conditions.

\* \* \* \* \*